(12) United States Patent
Shoji et al.

(10) Patent No.: US 9,107,747 B2
(45) Date of Patent: Aug. 18, 2015

(54) SOFT INTRAOCULAR LENS AND METHOD OF MANUFACTURING THE SAME

(75) Inventors: Noriyuki Shoji, Kitamoto (JP); Kikuo Mitomo, Honjo (JP)

(73) Assignee: Hoya Corporation, Tokyo (JP)

( * ) Notice: Subject to any disclaimer, the term of this patent is extended or adjusted under 35 U.S.C. 154(b) by 9 days.

(21) Appl. No.: 13/146,916

(22) PCT Filed: Feb. 17, 2010

(86) PCT No.: PCT/JP2010/052304
§ 371 (c)(1),
(2), (4) Date: Aug. 12, 2011

(87) PCT Pub. No.: WO2010/095628
PCT Pub. Date: Aug. 26, 2010

(65) Prior Publication Data
US 2011/0313520 A1    Dec. 22, 2011

(30) Foreign Application Priority Data

Feb. 20, 2009  (JP) .................................. 2009-038251
Feb. 20, 2009  (JP) .................................. 2009-038252

(51) Int. Cl.
*A61F 2/16* (2006.01)
*A61L 27/50* (2006.01)

(52) U.S. Cl.
CPC .............. *A61F 2/1613* (2013.01); *A61F 2/1662* (2013.01); *A61F 2002/1683* (2013.01); *A61L 27/50* (2013.01); *A61L 2430/16* (2013.01); *Y10T 83/04* (2015.04)

(58) Field of Classification Search
CPC ....... A61F 2/16; A61F 2/1613; A61F 2/1648; A61F 2002/1681; A61F 2002/1697; A61F 2002/1683; A61F 2/1662; A61L 27/50; A61L 2430/16

USPC .................... 623/6.18, 6.38–6.39, 6.43–6.45
See application file for complete search history.

(56) References Cited

U.S. PATENT DOCUMENTS 4,615,702 A    10/1986  Koziol
4,725,277 A     2/1988  Bissonette
(Continued)

FOREIGN PATENT DOCUMENTS

EP    0195881 A1    10/1986
EP    0413057 A1     8/1989
(Continued)

OTHER PUBLICATIONS

PCT International Search Report dated Mar. 16, 2010 for PCT App. Ser. No. PCT/JP2010/052304.
(Continued)

*Primary Examiner* — Howie Matthews
(74) *Attorney, Agent, or Firm* — Henricks, Slavin & Holmes LLP

(57) ABSTRACT

There is provided a soft intraocular lens, comprising: an optical lens section 10 made of a foldable soft material; and a support arm section 20 formed so as to protrude outward from an outer peripheral edge of the optical lens section 10 for holding the optical lens section 10 in an eye, wherein a tip end part 22 of the support arm section 20 is made of a different kind of material which is harder than a soft material of other portion of the soft intraocular lens 1, and adhesiveness of the tip end part 22 of the support arm section 20 is set to be lower than the adhesiveness of other portion of the soft intraocular lens 1.

27 Claims, 4 Drawing Sheets

(56) References Cited

U.S. PATENT DOCUMENTS

| | | | |
|---|---|---|---|
| 4,764,169 A | 8/1988 | Grendahl | |
| 5,015,254 A | 5/1991 | Greite | |
| 5,135,540 A | 8/1992 | Schepel | |
| 5,217,491 A * | 6/1993 | Vanderbilt | 623/6.46 |
| 5,266,241 A | 11/1993 | Parekh | |
| 5,589,024 A | 12/1996 | Blake | |
| 5,618,316 A | 4/1997 | Hoffmann | |
| 5,674,282 A * | 10/1997 | Cumming | 623/6.44 |
| 5,716,403 A | 2/1998 | Tran | |
| 6,193,750 B1 | 2/2001 | Cumming | |
| 6,224,628 B1 * | 5/2001 | Callahan et al. | 623/6.4 |
| 6,267,784 B1 | 7/2001 | Benz | |
| 6,310,215 B1 | 10/2001 | Iwamoto | |
| 6,342,073 B1 | 1/2002 | Cumming | |
| 6,387,127 B1 | 5/2002 | Muller-Lierheim | |
| 6,555,030 B1 | 4/2003 | Weinschenk | |
| 6,942,695 B1 | 9/2005 | Chapoy | |
| 7,160,488 B2 | 1/2007 | Ichikawa | |
| 7,223,288 B2 | 5/2007 | Zhang | |
| 7,632,431 B2 | 12/2009 | Ghazizadeh | |
| 2003/0158560 A1 | 8/2003 | Portney | |
| 2004/0111151 A1 * | 6/2004 | Paul et al. | 623/6.37 |
| 2009/0082861 A1 | 3/2009 | Marunaka | |
| 2010/0145446 A1 | 6/2010 | Shoji | |

FOREIGN PATENT DOCUMENTS

| | | |
|---|---|---|
| EP | 0 172 618 A2 | 2/2015 |
| FR | 2773705 A1 | 7/1999 |
| JP | 4-502586 A | 5/1992 |
| JP | 4-295353 A | 10/1992 |
| JP | 8-501480 | 2/1996 |
| JP | 9-276303 A | 10/1997 |
| JP | 10-043214 A | 2/1998 |
| JP | 10-85319 A | 4/1998 |
| JP | 10-192311 | 7/1998 |
| JP | 10-513099 A | 12/1998 |
| JP | 2000-290256 A | 10/2000 |
| JP | 2002-540828 A | 12/2002 |
| JP | 2003-511197 A | 3/2003 |
| JP | 2006-231066 A | 9/2006 |
| WO | WO 90/04512 A1 | 5/1990 |
| WO | WO95/01762 A | 1/1995 |
| WO | WO 97/20523 A1 | 6/1997 |
| WO | WO 00/59365 A | 10/2000 |
| WO | WO 01/28458 A | 4/2001 |
| WO | WO 2006/123428 A1 | 11/2006 |

OTHER PUBLICATIONS

European Supplementary Search Report dated May 26, 2015 for EPO App. Ser. No. 10 743 754.3.

* cited by examiner

SOFT INTRAOCULAR LENS AND METHOD OF MANUFACTURING THE SAME

TECHNICAL FIELD

The present invention relates to a soft intraocular lens inserted into an aphakic eye after cataract surgery, or a phakic soft intraocular lens inserted into an eye in a refractive surgical procedure, and particularly relates to an intraocular lens suitable for being inserted into the eye from a small incised wound in a folded state, and a manufacturing method of the same.

DESCRIPTION OF RELATED ART

For example, when a crystalline lens is clouded by cataract, recovery of a visual acuity is achieved by a surgical treatment of inserting an intraocular lens, being an artificial lens, into an eye, instead of the clouded crystalline lens. The intraocular lens used at this time has approximately a round or oval shaped optical lens section, and a support arm section (also called an "antennal part" because it is similar to antennal senses of insects), which extends outward from an outer peripheral edge of the optical lens section for making the optical lens section stable in the eye.

This kind of intraocular lens includes a hard intraocular lens with the optical lens section made of a hard material such as PMMA (polymethyl methacrylate-acrylic resin), and a soft intraocular lens with the optical lens section made of a soft material such as silicone elastomer and soft acryl.

When the hard intraocular lens is used, the lens needs to be inserted, by forming an incised wound on cornea or sclera, having approximately the same diameter and width as those of the optical lens section. Meanwhile, when the soft intraocular lens is used, it can be inserted from a smaller incised wound than a diameter of the optical lens section by folding the optical lens section.

In order to reduce corneal astigmatism and infection after surgery, the lens is preferably inserted from the smaller incised wound. Further, various injectors for inserting the intraocular lens from further smaller incised wound has been developed, and the soft intraocular lens which can be inserted from the smaller incised wound has been clinically used widely.

When the soft intraocular lens is roughly classified from a structural aspect, it can be classified into a type that the optical lens section and the support arm section are made of different kind of materials, and a type that the optical lens section and the support arm section are made of the same material.

The intraocular lens of a type that the optical lens section and the support arm section are made of different kind of materials, is generally composed of an approximately round shaped optical lens section made of a soft material such as foldable silicon, acrylic resin, or hydrogel, and the support arm section made of a hard material such as polypropylene or polymethylmethacrylate, which is relatively harder than the soft material, and for example the intraocular lens is obtained by attaching the support arm section to the optical lens section by bonding, etc., after fabricating the optical lens section. The support arm section is hard and has a tension, and therefore stability in the eye is relatively excellent. However, manufacturing steps are complicated, thus requiring high manufacturing cost, and trouble is possibly generated at a bonded place between the optical lens section and the support arm section in some cases.

Further, unlike a method of connecting the optical lens section and the support arm section integrally by bonding, etc., as described in the technique of patent document 1, there is provided a method of cutting a lens from a lens blank in which the soft material and the hard material are bonded to each other, and integrally fabricating the intraocular lens composed of a soft optical lens section and a hard support arm section.

However, in the intraocular lens obtained by a conventional method of this kind, an entire part from a bonded part to a tip end part of the support arm section is made of the hard material. Therefore, when the lens is folded and is inserted into an eye from the small incised wound by using the injector, there is a problem that the support arm section made of the hard material is broken or an unreasonable force is added to the bonded part of the support arm section, being a boundary part of different kind of materials, thus separating the support arm section from the bonded part or damaging the support arm section.

Meanwhile, as is shown in patent document 2, the intraocular lens of a type that the optical lens section and the support arm section are made of the same soft material, has no problem of the damaging, separating, or slipping-off of the support arm section, compared with the intraocular lens of a type that the optical lens section is made of the different kind of material from the kind of the support arm section. Further, this type of the intraocular lens is relatively simple in the manufacturing method, and therefore this type of the intraocular lens has been widely spread at present.

RELATED ART DOCUMENT

Patent Documents

Patent document 1:
Japanese Patent Laid Open Publication No. 1992-295353
Patent document 2:
Published Japanese Translation of a PCT application No. 1998-513099

SUMMARY OF THE INVENTION

Problem to be Solved by the Invention

Usually, when the soft intraocular lens of the aforementioned type, which is entirely composed of the soft material, is inserted into the eye, the lens is folded to be small so as to be accommodated in the injector and is inserted into the eye. For example, the optical lens section is folded into two, to interpose the tip end side of the support arm section therein, thereby inserting the lens into the injector, and in this state, the lens is inserted into the eye from a tip end opening of the injector. When the lens is inserted into the eye, the support arm section is developed in the eye together with the optical lens section, and recovered to an original shape. Therefore, there is an advantage that an inserting operation of the lens into the eye can be simplified.

However, in the conventional soft intraocular lens of this type, the support arm section is made of the same soft material as the material of the optical lens section. Therefore, when the optical lens section is folded into two to interpose the tip end side of the support arm section therein, the tip end of the support arm section sticks to the surface of the optical lens section, and a stuck portion of the support arm section is not naturally separated even after being inserted into the eye, thus frequently requiring an operation by an operator, to forcibly separate the support arm section from the optical lens section and stretch it into the original shape, thus causing a damage to occur in the lens during separating operation, and adding a strong stress to the operator even if not causing a damage in the lens.

In view of the above-described circumstance, the present invention is provided, and an object of the present invention is to provide a soft intraocular lens capable of reducing a load of the operator, and a manufacturing method of the same.

Means for Solving the Problem

In order to solve the above-described problem, a first aspect of the present invention provides a soft intraocular lens, comprising:
an optical lens section made of a foldable soft material; and
a support arm section formed so as to protrude outward from an outer peripheral edge of the optical lens section for holding the optical lens section in an eye,
wherein adhesiveness of a tip end part of the support arm section is set to be lower than the adhesiveness of other portion of the soft intraocular lens.

A second aspect of the present invention provides a soft intraocular lens, comprising:
an optical lens section made of a foldable soft material; and
a support arm section formed so as to protrude outward from an outer peripheral edge of the optical lens section for holding the optical lens section in an eye,
wherein a tip end part of the support arm section is made of a different kind of material which is harder than the soft material of other portion of the soft intraocular lens.

A third aspect of the present invention provides the soft intraocular lens according to the second aspect, wherein a boundary part between the hard material that forms the tip end part of the support arm section, and the soft material that forms a base end side portion of the support arm section on an inner peripheral side of the tip end part, being other portion of the soft intraocular lens, and forms the optical lens section, is provided outside of a circle having radius of 5 mm, with a center of the optical lens section as a center.

A fourth aspect of the present invention provides the soft intraocular lens according to the second or third aspect, wherein the soft material that forms a based end side portion of the support arm section, being other portion of the soft intraocular lens, and forms the optical lens section, is colorless and transparent or pale-colored and transparent, and the hard resin that forms the tip end part of the support arm section is made of a colored material with higher visibility than the visibility of the soft material.

A fifth aspect of the present invention provides the soft intraocular lens according to any one of the second to fourth aspects, wherein the hard material is hard plastic mainly composed of PMMA (polymethylmethacrylate-acrylic resin).

A sixth aspect of the present invention provides the soft intraocular lens according to any one of the second to fifth aspects, wherein a narrowest portion of a width of the support arm section is 0.2 mm or more.

A seventh aspect of the present invention provides a manufacturing method of the soft intraocular lens according to any one of the second to sixth aspects, wherein the soft intraocular lens is obtained, with the tip end part of the support arm section made of a hard material, and a base end side portion of the support arm section on an inner peripheral side of the tip end part, being other portion of the soft intraocular lens, and the optical lens section, made of a soft material, by applying mechanical machining to a cylindrical rod in which the soft material is arranged on the inner peripheral side and the hard material is arranged on an outer peripheral side concentrically.

Advantage of the Invention

According to the present invention, there is provided a soft intraocular lens capable of reducing a load of an operator, and a manufacturing method of the same.

BEST MODE FOR CARRYING OUT THE INVENTION

Preferred embodiments of the present invention will be described hereafter, with reference to the drawings.

Figure 1A:
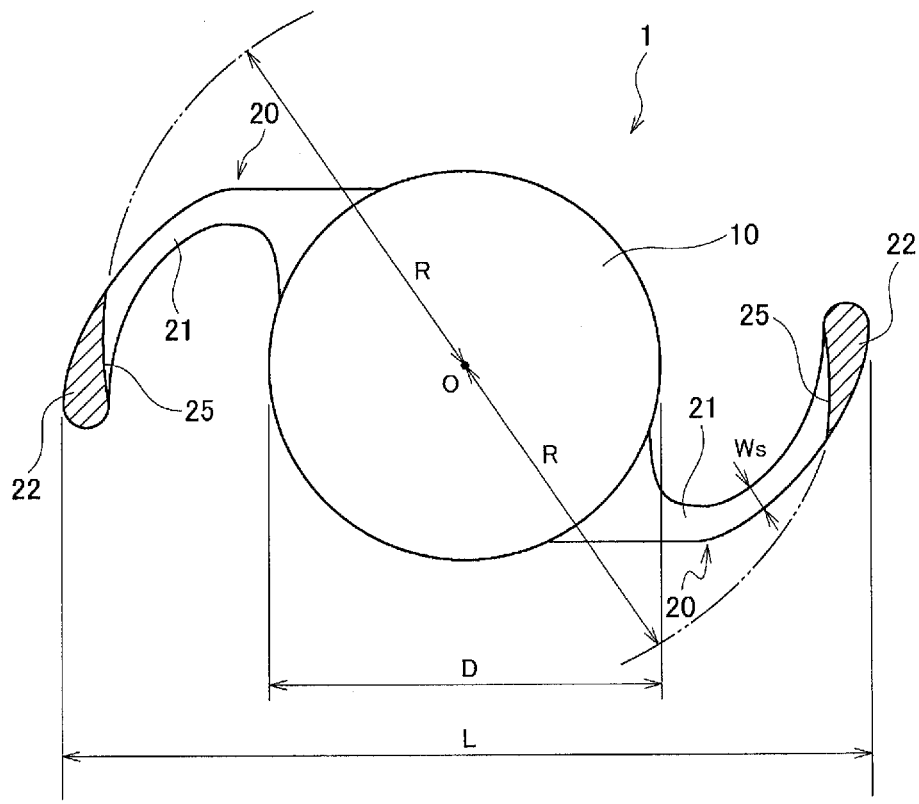
FIGS. 1A and 1B are plan and side views of a soft intraocular lens according to an embodiment of the present invention.
Figure 1B:
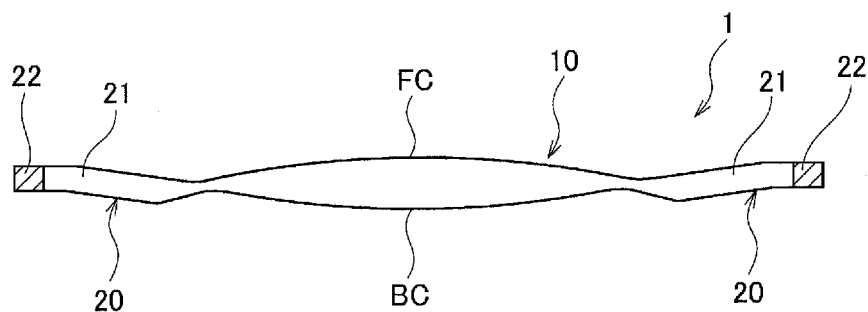
Figure 2:
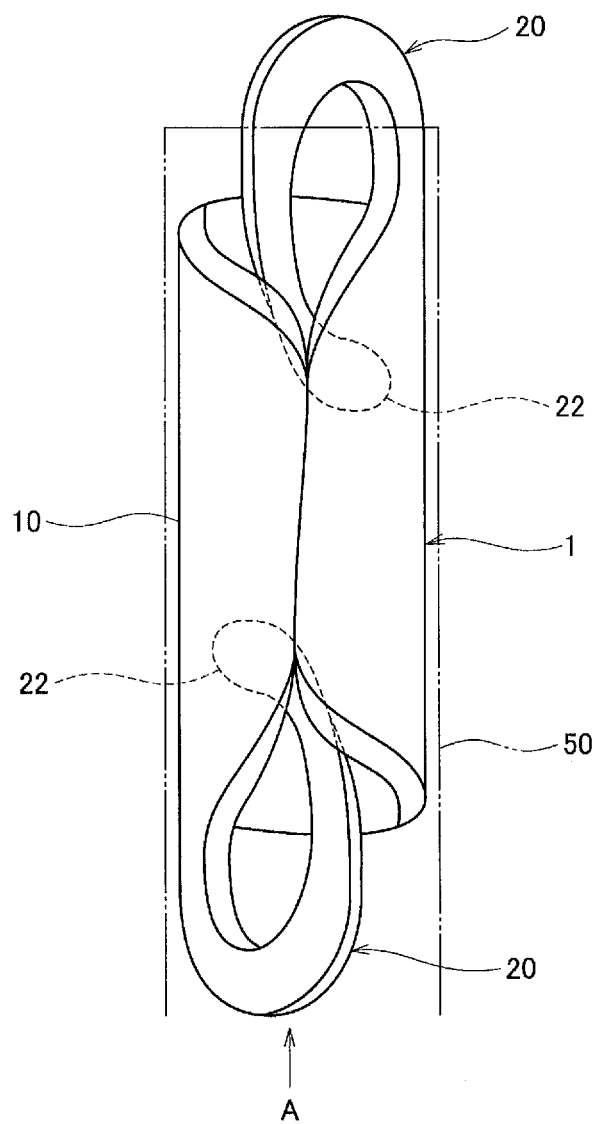
FIG. 2 is a view showing the soft intraocular lens in a state of being folded and inserted inside of a cartridge of an injector.

FIG. 1A is a plan view of a soft intraocular lens according to an embodiment of the present invention, FIG. 1B is a side view thereof, and FIG. 2 is a side view showing the soft intraocular lens of an embodiment in a state of being folded and inserted into a cartridge of an injector.

As shown in FIG. 1, the soft intraocular lens 1 (also called an "intraocular lens" or simply called a "lens" hereafter) has an optical lens section 10 made of a foldable soft material, and two curved shaped support arm sections 20 (or "haptics") formed in such a manner as protruding outward from an outer peripheral edge of the optical lens section 10. The optical lens section 10 is formed as a round shaped convex lens.

The support arm section 20 holds and fixes the optical lens section 10 in an eye, and two support arm sections 20 are provided in a point-symmetric positional relation, with a center O of the optical lens section 10 as a symmetric center. Two support arm sections 20 are curved in the same direction (counterclockwise in FIG. 1A), and front and back of the lens 1 can be discriminated by the direction of the curve.

A base end side portion 21 on an inner peripheral side of the tip end part 22 of the support arm section 20 is made of the same material as the material of the optical lens section 10. However, only the tip end part 22 is made of a different kind of material. Namely, only the tip end part 22 of the support arm section 20 is made of a different kind of material which is harder than the soft material of other portion of the soft intraocular lens 1. Here, other portion of the soft intraocular lens 1, namely, the base end portion 21 of the support arm section 20 and the optical lens section 10 is made of soft materials such as soft acrylic materials, silicon-based materials, hydrogel, and urethane materials, and the tip end part 22 of the support arm section 20 is made of plastic materials (hard materials) which are harder than the aforementioned soft materials and mainly composed of polymethyl methacrylate (PMMA) for example. Thus, only the tip end part 22 of the support arm section 20 is made of the hard material, and adhesiveness of the tip end part 22 of the support arm section 20 is set to be lower than the adhesiveness of the base end side portion 21 of the support arm section 20 on the inner peripheral side of the tip end part 22 and the optical lens section 10. Note that the intraocular lens 1 is formed so that a part from the optical lens section 10 to the tip end part 22 of the support arm section 20 is integrally formed, and the intraocular lens 1 thus formed corresponds to an intraocular lens called a so-called one piece type.

Note that in this specification, the "adhesiveness" means a property that a member is adhered or adsorbed to/on the other member when these members are brought into contact with each other, which is the property "easy to adhere".

A full length L (distance from the tip end of one of the support arm sections to the tip end of the other support arm section) of the intraocular lens 1 may be set to any dimension, provided that it is suitable. However, the full length L is preferably set to be in a range from 1 mm to 14 mm and most preferably set to be 12.5 mm. The optical lens section 10 has a front surface (FC surface) 11 and a back surface (BC surface) 12, and a diameter D thereof may be set to any dimension, provided that it is a suitable value, and is preferably set to be in a range from 5 mm to 7 mm, and most preferably set to 6 mm. Note that a thickness of the optical lens section 10 is varied depending on a desired refractive power and a refractive index of a used material.

The shape of the support arm section 20 may be set to any shape, provided that it is a curved shape capable of making the intraocular lens 1 stable in the eye after being inserted into the eye. However, in order to keep a restoring force of the support arm section after being inserted into the eye, the width of the support arm section 20 is preferably set to 0.2 mm or more in a narrowest portion Ws.

Further, R in FIG. 1(a) indicates a radius of a circle, with a center O of the optical lens section 10 as a center, and the tip end part 22 of the support arm section 20 which is made of a hard material, is preferably provided outside of a circle of R=5 mm. In other words, an arcuate boundary part 25 between the hard material that forms the tip end part 22 of the support arm section 20, and the soft material that forms the base end side portion 21 of the support arm section 20 on the inner peripheral side of the tip end parts 22 and the optical lens section 10, is preferably provided outside of the circle having radius of 5 mm, with the center O of the optical lens section 10 as a center. The width of the tip end part 22 varies along the arcuate length of the boundary part 25, as can be seen in FIG. 1(a). As illustrated in FIG. 1(b), the thickness of the base end side portion 21 is the same as the thickness of the tip end part 22 at the boundary part 25.

With this structure, as shown in FIG. 2, when the optical lens section 10 is folded into two to interpose the support arm section 20 therein so that the intraocular lens 1 is inserted into the cartridge 50 of the injector, the vicinity of the tip end part of each support arm section 20, being a necessary part for inserting the intraocular lens into the optical lens section 10, can be made of the hard material, and the hard portion is not unnecessarily made large. Accordingly, when the lens 1 is inserted into the eye by using a small bore injector, a risk of clogging of the lens 1 inside of the injector can be reduced, which is caused by a size of the tip end part 22 made of the hard material.

When a hard area is expanded to inside of the circle having radius of 5 mm, the ratio of the hard part occupying the support arm section 20 is increased, thus posing a high possibility of breakage or separation of the support arm section 20.

According to the intraocular lens 1 of this embodiment having the aforementioned structure, only the tip end part 22 of the support arm section 20 is made of the hard material. Therefore, as shown in FIG. 2, when the lens 1 is folded to be inserted into the eye by using the injector, the tip end part 22 is hardly stuck to a surface of the optical lens section 10, even if the tip end part 22 of the support arm section 20 is brought into contact with the surface of the optical lens section 10. Thus, the support arm section 20 is easily developed into an original shape after being inserted into the eye, by pushing the lens 1 out of the cartridge 50 of the injector as shown by arrow A in FIG. 2, and therefore the load of an operator can be reduced. Further, the base end side portion 21 of the support arm section 20 is made of the same soft material as the material of the optical lens section 20, and therefore substantially, the optical lens section 10 and the support arm section 20 function as the same soft intraocular lens, and therefore unlike the intraocular lens of a conventional type wherein an overall support arm section is made of the hard material, the problem of the breakage, slipout, or separation of the support arm section 20 can be reduced.

Further, in the intraocular lens 1, if hard resin that forms the tip end part 22 of the support arm section 20 is made of a colored material for improving visibility, the visibility of the intraocular lens 1 itself can be improved, major portion of which is colorless and transparent or pale-colored and transparent, thus making it easy to handle the intraocular lens 1. Further, confirmation of a state of folding the lens 1, and confirmation of a position of the tip end part 22 of the support arm section 20 when the intraocular lens 1 is inserted into the eye, are easy. This contributes to improving a success rate of an operation of lens insertion. Namely, the position of the tip end part 22 of the support arm section 20 can be easily confirmed by coloring, and therefore whether or not the support arm section 20 is folded can be easily judged. Note that the tip end parts 22 of the two support arm sections 20 may have different colors, such as red and blue.

Note that in this embodiment, explanation is given for a case that the resin is made of a hard material and is also made of a colored material. Meanwhile, the resin may be made of the colored material, even if not being made of the hard material. Specifically, the soft material that forms the base end side portion 21 of the support arm section 20 and the optical lens section 10 is made of colorless and transparent or pale-colored and transparent material, and the tip end part 22 of the support arm section 20 is made of a colored material that improves the visibility better than other portion of the soft intraocular lens 1. Thus, the tip end part 22 and the other portion can be easily discriminated by the operator, with a result that the load of the operator can be reduced.

Further, with this structure, as shown in FIG. 2, in order to insert the intraocular lens 1 into the cartridge 50 of the injector, only a required tip end portion to be interposed into the optical lens section 10 can be made of the colored material, when the optical lens section 10 is folded into two to interpose the support arm section 20 therein. Accordingly, the position of the tip end part 22 of the support arm section 20 can be easily confirmed during insertion of the intraocular lens, and even when compared with the intraocular lens with overall colored support arm section 20, whether or not the support arm section 20 is correctly folded can be easily judged. As a result, the load of the operator can be reduced.

Further, when the portion made of the colored material exists outside of the circle with radius of 5 mm, with the center of the optical lens section 10 as a center, the position of the tip end part 22 of the support arm section 20 can be easily confirmed when the intraocular lens is inserted into the eye, and this contributes to improving the success rate of a lens inserting operation. Namely, the position of the tip end part 22 of the support arm section 20 can be easily confirmed by coloring this part, and therefore even when compared with the intraocular lens with overall support arm section 20 colored, whether or not the support arm section 20 is correctly folded can be further easily judged.

Further, hard plastic mainly composed of PMMA is used for the intraocular lens 1 as the hard material, and therefore the intraocular lens with high stability in a living body can be provided at a relatively low cost.

Several advantages of this embodiment will be described in detail hereafter, in comparison with a conventional art.

A hydrophobic acrylic material is generally used as a soft intraocular lens material, from a viewpoint of a suitable shape restoring speed after insertion into the eye, the stability of the material in the eye, and the refractive index of the material. Generally, the hydrophobic acrylic material has a strong adhesiveness. Therefore, in a case of an operation of interposing the support arm section inside of the optical lens section which is folded into two during insertion into the eye, materials with strong adhesiveness are stuck to each other, thus hardly separated even after insertion into the eye, and hardly restored to the original shape in some cases.

In view of this point, according to this embodiment, the adhesiveness of the tip end part of the support arm section is made weaker than the adhesiveness of the base end side portion of the support arm section and the adhesiveness of the optical lens section (the adhesiveness is set to be low). Therefore, when the lens is folded and is inserted into the eye by using the injector, the tip end part is hardly stuck to the surface of the optical lens section even if the tip end part of the support arm section is brought into contact with the surface of the optical lens section.

Conventionally, when the tip end part is stuck to the surface of the optical lens section, the stuck portion of the support arm section is not naturally separated even after being inserted into the eye, and therefore the operator sometimes has to forcibly separate the support arm section from the optical lens section and stretch it to the original shape. This is a factor of damaging the lens when the tip end part is separated, and further is a factor of adding a strong stress to the operator even if not damaging the lens. However, according to this embodiment, such a trouble can be reduced.

Further, by forming the tip end part of the support arm section by the hard material, when the lens is folded to be inserted into the eye by using the injector, the tip end part of the support arm section is hardly stuck to the surface of the optical lens section even if the tip end part of the support arm section is brought into contact with the surface of the optical lens section. When it is already stuck to the surface of the optical lens section, the stuck portion of the support arm section is hardly separated even after being inserted into the eye. Therefore, it is sometimes necessary for the operator to forcibly separate the support arm section from the optical lens section and stretch it to the original shape. This causes a damage to be added to the lens during separating operation, and causes a strong stress to be added to the operator even if the damage is not added to the lens. Such a trouble can be reduced. Further, the base end side portion of the support arm section is made of the same soft material as the material of the optical lens section, and therefore the problem of damaging, separating, or slipping-off of the support arm section can be reduced, unlike the intraocular lens of a conventional type in which the support arm section is made of the hard material.

Further, the portion made of the hard material exists outside of the circle with radius of 5 mm, with the center of the optical lens section as a center. Therefore, the portion made of the hard material is not made unnecessarily large. Accordingly, when the lens is inserted into the eye by using a small bore injector, the risk of clogging the lens inside of the injector due to the size of the hard material portion can be reduced. Namely, flexibility of the base end side portion of the support arm section can be sufficiently secured, and therefore possibility of the clogging can be reduced.

Note that generally the full length of the intraocular lens (distance from the tip end of one of the support arm sections to the tip end of the other support arm section, when the support arm section is provided symmetrically outside of the optical lens section) is 12 mm or more, and when the tip end part of the hard support arm section is provided inside of the circle with radius of 5 mm, with the center of the optical lens section as a center, the ratio of the hard portion occupying the support arm section is increased, and the possibility of damaging and separating the support arm section is also increased. Further, when the support arm section is inserted into the injector, bending performance of the support arm section is influenced by the hard portion, thus generating a possibility that the support arm section is hardly bent suitably. However, in an example of this embodiment, generation of the aforementioned phenomenon can be prevented by setting the range of the hard portion, outside of the circle with radius of 5 mm.

An embodiment of the manufacturing method of the intraocular lens 1 with the aforementioned structure will be described next.

Figure 3A:
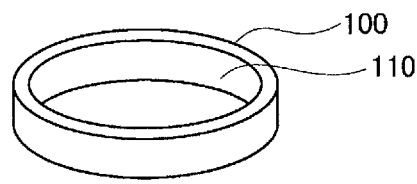
FIGS. 3A to 3D are explanatory views of manufacturing steps of the intraocular lens.

In the manufacturing method of this embodiment, first, as shown in FIG. 3A, there is provided a hard portion forming member (also called a hard material hereafter) 100 formed into approximately a donut shape made of PMMA. For example, a circular hole 110 is opened in a center of a button material which is formed by molding colored PMMA into approximately a disc shape, to thereby obtain the hard portion forming member 100.

Figure 3B:
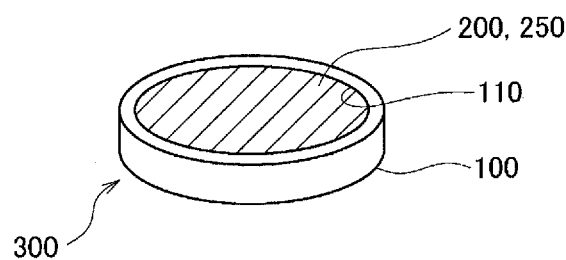

Next, a raw material liquid 200, becoming a soft acryl after polymerization is injected into the circular hole 110 in the center of the hard portion forming member 100, to thereby complete the polymerization. Thus, as shown in FIG. 3B, a disc-shaped raw material 300 is obtained, in which a soft material 250 forming the optical lens section 10 and the base end side portion 21 of the support arm section 20, and the hard portion forming member (hard material) 100 forming the tip end part 22 of the support arm section 20 are integrally formed.

Figure 3C:
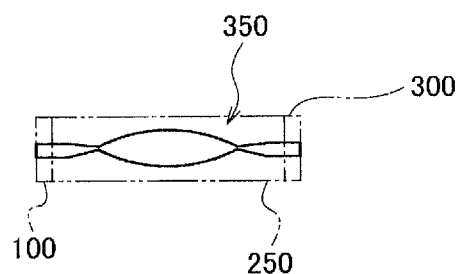

Next, as shown in FIG. 3C, surface forming machining is applied to front and rear surfaces of the disc-shaped raw material 300 by using precision lathe equipment. Thus, a disc-shaped intermediate member 350 in plan view having the surface and rear surface shape of the intraocular lens is obtained. When the surface forming machining is applied by using the precision lather equipment, the hard portion forming member 100 can be grasped. Therefore, positioning with high precision is realized, thus facilitating the machining.

Figure 3D:
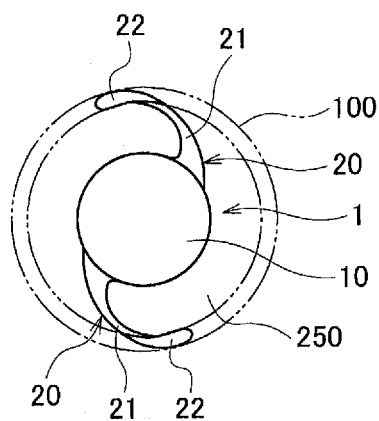

Next, as shown in FIG. 3D, a profile shown by solid line is formed by using milling equipment. Finally, polishing is applied thereto, to thereby obtain the intraocular lens 1 of one piece type as shown in FIGS. 1A and 1B.

According to the manufacturing method of the intraocular lens of this embodiment, an advantage as described below is exhibited.

Namely, the intraocular lens with only a part (tip end part of the support arm section) formed by a different kind of material can be easily manufactured with high precision. At this time, the soft portion (the base end side portion of the support arm section, and the optical lens section) can be machined, with an outer peripheral side hard portion as a support. Therefore, manufacture can be facilitated.

Here, specific dimension examples of the intraocular lens shown in FIGS. 1A and 1B are as follows. The full length L is for example 12.5 mm, a diameter D of the optical lens section 10 is for example 6 mm, a central thickness of the optical lens section 10 is for example 0.7 mm, narrowest portion (Ws) of the width of the support arm section 20 is for example 0.4 mm, the thickness of the support arm section 20 at this portion is for example 0.4 mm, and the hard tip end portion 22 is provided outside of the circle with radius of R=5.55 mm, and its thickness is for example 0.4 mm.

In addition, silicon-based materials, hydrogel, and urethane-based materials, etc., can be given as examples of the soft material of the optical lens section 10 and the support arm section 20, and hard acrylic materials, polyimide, and polypropylene, etc., can be given as examples of the hard material. Of course, a coloring agent and an ultraviolet absorber may be arbitrarily added to each material.

Figure 4:
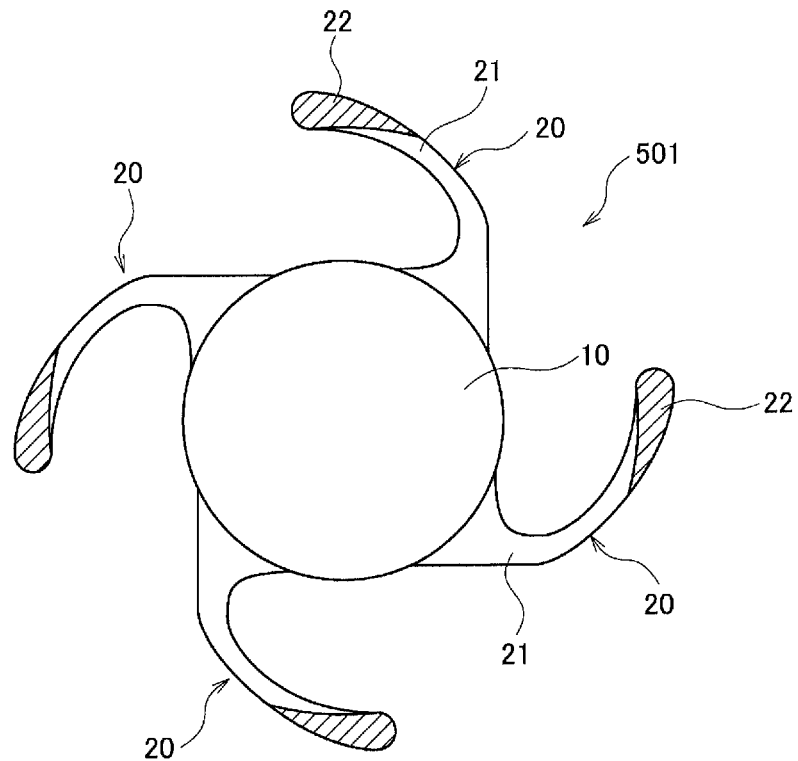
FIG. 4 is a plan view of the soft intraocular lens according to other embodiment of the present invention.

FIG. 4 shows a structure of a soft intraocular lens 501 according to other embodiment of the present invention. In the intraocular lens 501, four support arm sections 20 are provided around the optical lens section 10, and each tip end part 22 of the support arm section 20 is made of the hard material, and the optical lens section 10 and the base end side portion 21 of the support arm section 20 are made of the soft material.

Figure 5:
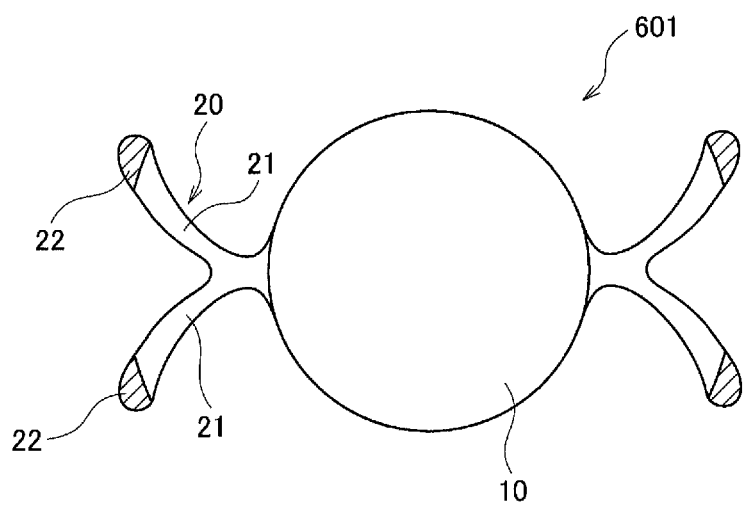
FIG. 5 is a plan view of the soft intraocular lens according to further other embodiment of the present invention.

Further, FIG. 5 shows a structure of the soft intraocular lens 601 according to other embodiment of the present invention. In the intraocular lens 601, the support arm section 20 is biforcately formed at a symmetrical position on the outer periphery of the optical lens section 10, wherein each tip end part 22 of the support arm section 20 is made of the hard material, and the optical lens section 10 and the base end side portion 21 of the support arm section 20 is made of the soft material.

By thus forming the tip end part 22 of the support arm section 20 by the hard material, the support arm section 20 is hardly stuck to the surface of the optical lens section 10, and a similar effect as the effect of the embodiment shown in FIGS. 1A and 1B is exhibited.

In the aforementioned embodiment, by forming the material of the tip end part 22 of the support arm section 20 by the hard material, adhesiveness of the tip end part 22 is reduced. However, surface texturing can be applied to only the tip end part 22, so that adhesiveness is simply reduced.

Further, the manufacturing method of the intraocular lens 1 of one piece type can also be utilized when machining the intraocular lens made of a single material with high precision, the single material being the soft material extending to the tip end part 22 of the support arm section 20. In this case, the hard material 100 around the soft material 250 integrally formed with the soft material 250, is not a constituent member of the intraocular lens. However, the hard portion forming member 100 can be thereby grasped during surface forming machining, and therefore surface formation with high precision is realized.

DESCRIPTION OF SIGNS AND NUMERALS

1 Intraocular lens
10 Optical lens section
20 Support arm section
21 Base end side portion
22 Tip end part
25 Boundary part
50 Injector cartridge
100 Hard portion forming member (hard material)
250 Soft material

What is claimed is:

1. An intraocular lens, comprising:
an optical lens section made of a foldable first material and configured to be folded in half such that first and second portions of the optical lens section face one another; and
a support arm section formed so as to protrude outward from an outer peripheral edge of the optical lens section for holding the optical lens section in an eye, the support arm section including an outer surface and a thickness, a base end side portion formed from the first material and a tip end part,
wherein the base end side portion and the tip end part meet on the outer surface at a boundary that extends completely through the thickness of the support arm section, the first material is not located radially outward of the boundary, the tip end part is made of a second material which is harder than the first material, the second material is not located radially inward of the boundary; and
wherein the support arm section is configured such that the tip end part may be positioned between the first and second portions of the optical lens section when the optical lens section is folded in half.

2. The soft intraocular lens according to claim 1, wherein the boundary is provided outside of a circle having radius of 5 mm, with a center of the optical lens section as a center.

3. The soft intraocular lens according to claim 1, wherein the second material is plastic mainly composed of PMMA (polymethyl methacrylate-acrylic resin).

4. The soft intraocular lens according to claim 1, wherein a narrowest portion of a width of the support arm section is 0.2 mm or more.

5. The soft intraocular lens according to claim 2, wherein the second material is plastic mainly composed of PMMA (polymethyl methacrylate-acrylic resin).

6. The soft intraocular lens according to claim 2, wherein a narrowest portion of a width of the support arm section is 0.2 mm or more.

7. The soft intraocular lens according to claim 3, wherein a narrowest portion of a width of the support arm section is 0.2 mm or more.

8. An intraocular lens, comprising:
an optic formed from a foldable first material and including an outer peripheral edge and defining an optic center; and
an open loop haptic defining a base end that abuts the optic outer peripheral edge, a tip end opposite the base end and a curvilinear centerline that extends from the base end to the tip end, and including a first portion that extends from the base end toward tip end and terminates at a boundary that is entirely located a single radial distance R that extends in a radial direction from the optic center and defines an arcuate boundary length and a second portion that extends from the boundary to the tip end, wherein the haptic is formed solely from the first material from the base end to the boundary and is formed solely from a second material that is harder than the first material from the boundary to the tip end and the second material defines a width extending from the boundary in the radial direction that varies in magnitude along the arcuate boundary length.

9. An intraocular lens as claimed in claim 8, wherein
the haptic defines a haptic length that extends from the base end to the tip end; and
the first portion of the haptic occupies more of the haptic length than the second portion of the haptic.

10. An intraocular lens as claimed in claim 8, wherein the boundary is at least 5 mm from the optic center.

11. An intraocular lens as claimed in claim 8, wherein the second material is a plastic.

12. An intraocular lens as claimed in claim 8, wherein the haptic defines a haptic length that extends from the base end to the tip end; and
the haptic defines a width that is at least 0.2 mm over the haptic length.

13. An intraocular lens, comprising:
an optic formed from a foldable first material and including and optic center and an outer peripheral edge; and
a haptic defining a base end that abuts the optic outer peripheral edge, a tip end opposite the base end, a curvilinear centerline that extends from the base end to the tip end in such a manner that a point on the centerline at the tip end is rotationally offset about the optic center from a point on the centerline at the base end, a front surface, a back surface, a thickness that extends from the front surface to the back surface, and including a first portion that extends from the base end toward tip end formed solely from the first material and a second portion that extends from the tip end toward the base end formed solely from a second material that is harder than the first material, the first and second portions of the haptic having respective ends that meet at a boundary that is located between the first and second portions, extends through the haptic and is where the first material meets the second material on the exterior surface, the thickness of the end of the first portion of the haptic being equal to the thickness of the end of the second portion of the haptic.

14. An intraocular lens as claimed in claim 13, wherein the haptic defines a haptic length that extends from the base end to the tip end; and
the first portion of the haptic occupies more of the haptic length than the second portion of the haptic.

15. An intraocular lens as claimed in claim 13, wherein the optic defines a center; and
the boundary is at least 5 mm from the optic center.

16. An intraocular lens as claimed in claim 13, wherein the second material is a plastic.

17. An intraocular lens as claimed in claim 13, wherein the haptic defines a haptic length that extends from the base end to the tip end; and
the haptic width is at least 0.2 mm over the haptic length.

18. The soft intraocular lens according to claim 1, wherein the support arm section comprises an open loop haptic.

19. An intraocular lens as claimed in claim 13, wherein the haptic comprises an open loop haptic.

20. The intraocular lens according to claim 1, wherein the first material is colorless and transparent or pale-colored and transparent, and the second material is made of a colored material with higher visibility than the visibility of the first material.

21. The intraocular lens according to claim 2, wherein the first material is colorless and transparent or pale-colored and transparent, and the second material is made of a colored material with higher visibility than the visibility of the first material.

22. The intraocular lens according to claim 20, wherein the second material is plastic mainly composed of PMMA (polymethyl methacrylate-acrylic resin).

23. The intraocular lens according to claim 20, wherein a narrowest portion of a width of the support arm section is 0.2mm or more.

24. An intraocular lens as claimed in claim 8, wherein the first material is transparent and has a first visibility; and
the second material is a colored and has a second visibility that is greater than the first visibility.

25. An intraocular lens as claimed in claim 8, wherein the first material has a first adhesiveness; and
the second material has a second adhesiveness that is less than the first adhesiveness.

26. An intraocular lens as claimed in claim 13, wherein the first material is transparent and has a first visibility; and
the second material is a colored and has a second visibility that is greater than the first visibility.

27. An intraocular lens as claimed in claim 13, wherein the first material has a first adhesiveness; and
the second material has a second adhesiveness that is less than the first adhesiveness.

* * * * *